(12) United States Patent
Griffiths et al.

(10) Patent No.: US 6,458,460 B1
(45) Date of Patent: *Oct. 1, 2002

(54) WOUND DRESSING

(75) Inventors: Bryan Griffiths, Chester; Elizabeth Jacques, Hoole; Stephen Bishop, Deeside, all of (GB)

(73) Assignee: Bristol-Myers Squibb Company, Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/254,323

(22) PCT Filed: Sep. 5, 1997

(86) PCT No.: PCT/EP97/04927

§ 371 (c)(1),
(2), (4) Date: Nov. 15, 1999

(87) PCT Pub. No.: WO98/09590

PCT Pub. Date: Mar. 12, 1998

(51) Int. Cl.[7] .................................................. B32B 27/00
(52) U.S. Cl. .............................. 428/425.1; 428/311.71; 428/342; 428/377; 602/56; 442/333; 442/403; 442/405; 442/411; 442/414; 442/415; 442/416

(58) Field of Search ........................... 428/311.71, 342, 428/377, 425.1; 442/333, 403, 405, 411, 414, 415, 416; 602/56, 41, 42, 43, 48, 52, 54

(56) References Cited

U.S. PATENT DOCUMENTS

| | | | | | |
|---|---|---|---|---|---|
| 5,445,826 A | * | 8/1995 | Kuhrts | ........................ | 424/451 |
| 5,550,189 A | * | 8/1996 | Qin et al. | ................... | 525/54.3 |
| 6,075,117 A | * | 6/2000 | Bahia et al. | .................. | 602/43 |
| 9,153,214 | * | 11/2000 | Horsler | ........................ | 424/443 |

FOREIGN PATENT DOCUMENTS

| | | | | | |
|---|---|---|---|---|---|
| DE | 43 28 329 A | * | 8/1993 | ............. | C08L/5/00 |
| EP | 0 651 983 A1 | * | 10/1995 | ........... | A61L/13/00 |
| EP | 0 691 133 A1 | * | 10/1996 | ........... | A61L/15/60 |
| WO | 96/10106 | * | 8/1993 | ............. | D01F/9/04 |
| WO | 98/46818 | * | 10/1998 | ........... | D04B/21/16 |

* cited by examiner

*Primary Examiner*—Terrel Morris
*Assistant Examiner*—Arti R. Singh
(74) *Attorney, Agent, or Firm*—John M. Kilcoyne

(57) ABSTRACT

A wound dressing comprises a blend of at least two types of discrete fibers wherein one discrete fiber is of a modified cellulose gel-forming material and a second discrete fiber is of another type of gel-forming material such as an alginate.

10 Claims, No Drawings

WOUND DRESSING

This invention relates a wound dressing and in particular a non-adherent wound dressing comprising fibrous material.

The invention also relates to a method of treating a wound comprising applying the dressing to a wound.

It is well known that the cleansing and debriding of wounds and the removal of wound exudate is important to the process of healing wounds. Commonly used wound dressings comprise gauze, foams, sponges, cotton wads or other fibrous materials. Gauze and other fibrous materials absorb fluids by capillary action. Some absorbent fibres are capable of forming a gel on contact with exudate which can give the advantage of non-adherence to the wound. Such fibres when used alone in contact with a wound tend to preferentially absorb a particular type of exudate. In addition such fibres when used alone in contact with a wound tend to be capable of absorbing exudate at only one rate or in one rate pattern. For instance those fibres based on cellulose tend show high absorptive capacity for water which tends to be initially very high and then tail off. Since wound exudates are variable and can have different ion contents and viscosities optimum treatment of a particular wound is not always achieved when such fibres are used alone.

WO 96/10106 relates to fibres which are useful in wound dressings which comprise alginate co-spun with at least one water soluble species other than alginate. The fibres although of composite type, are used alone and may not achieve optimum treatment of a particular wound.

We have now found that the disadvantages of the prior art can be mitigated by mixing different types of gelling fibres together. Accordingly the present invention provides a wound dressing comprising, in sheet form, a mixture of different types of gel forming fibres.

The wound dressing according to the invention may have the advantages that it provides good absorbency for a range of exudates and is also relatively inexpensive. In addition a moist wound environment may be created which has been found to be beneficial to wound healing.

The gel forming fibres for use in the present invention are hygroscopic fibres which upon the uptake of wound exudate become moist and slippery or gelatinous and thus reduce the tendancy for the surrounding fibres to adhere to the wound. The gel forming fibres can be of the type which retain their structural integrity on absorbtion of exudate or can be of the type which lose their fibrous form and become a structureless gel or a solution on absorption of exudate.

The gel forming fibres are preferably spun sodium carboxymethylcellulose fibres, chemically modified cellulosic fibres, in particular carboxymethylated cellulose fibres as described in PCT WO/9312275 to Courtaulds Plc or GB93/01258 to Courtaulds Plc, pectin fibres, alginate fibres and particularly those as described in WO94/17227 to E. R. Squibb and Sons or EP 433354 to CV Laboratories Ltd or EP 476756 to CV Laboratories Ltd, chitosan fibres, hyaluronic acid fibres, or other polysaccharide fibres or fibres derived from gums. The cellulosic fibres preferably have a degree of substitution of at least 0.05 carboxymethyl groups per glucose unit. The production of solvent-spun cellulose fibres is described for example in U.S. Pat. Nos. 4,246,221 and 4,196,281 as well as in PCT WO/9312275 mentioned above.

Preferably the gel forming fibres for use in the present invention have an absorbency of either water or saline of at least 15 g/g as measured in the free swell absorbency method, more preferably at least 25 g/g or 50 g/g. The degree of substitution of the gel forming fibre is preferably at least 0.2 carboxymethyl groups per glucose unit, more preferably between 0.3 and 0.5. The tenacity of the fibre is preferably in the range 25–15 cN/tex.

The gel forming fibres are preferably mixed to give a dressing comprising fibres of different absorbencies and also different absorbency rates and profiles.

The dressing may comprise other fibres such as textile fibres which can be natural or synthetic but are preferably cellulosic fibres for example viscose rayon, multi-limbed viscose, cotton, or regenerated cellulose or fibres having a higher absorbency than most textile fibres such as the multi-limbed cellulose fibres as described in EP-A-301874. In general textile fibres absorb liquids by capilliary action and are not hygroscopic this means that their absobancies as measured by the free swell absorbency test are low such as less than 1 gram of liquid per gram of fibre.

More preferably the dressing comprises a blend of gel forming alginate fibres and cellulosic fibres in the range of 50% to 95% of alginate fibres and 5% to 50% of modified cellulose fibres by weight. Preferably the dressing comprises a blend of fibres in the range of 65% to 80% alginate fibres and 20% to 35% modified cellulose fibres by weight and most preferably 30% modified cellulose fibres and 70% alginate fibres by weight.

The gel forming fibres suitable for use in the present invention can be processed using conventional textile machinery, for example by the staple route including cutting, carding and if desired crimping, drafting and spinning.

The wound dressing of the present invention may be in sheet form and may be made by intimately mixing the gel forming fibres, for example by carding, air-laying or needle punching the fibres together to form a web of mixed fibres. Alternatively the wound dressing of the present invention may be made by spinning or twisting the gel forming fibres together to form a yarn and then knitting or weaving the yarn to form a bandage or stocking. The wound dressing of the present invention may be in the form of swabs, wound pads, wadding ribbons, sponges, nets and bandages with the fibrous layer being one of many layers and may be used as a primary or secondary dressing especially in the treatment of leg ulcers.

Various optional ingredients can also be included in the final composition such as preservatives and small amounts of pharmacologically active ingredients. For example an antibiotic or antimicrobial agent such as metronidazole, silver sulphadiazine, neomycin or penicillin and antiseptic agent such as povidone iodine and antiinflammatory agent such as hydrocortisone or triamcinolone actenoide or a skin protective agent such as a zinc oxide can be included. The invention is illustrated by the following examples:

EXAMPLE 1

A dressing according to the invention was made by cutting fibres to a staple length of approximately 50 mm. The alginate fibres were of the type described in EP 43 354 or EP 476 756 to CV Laboratories Ltd and sold as a fibrous dressing in the product KALTOSTAT ex ConvaTec and the cellulose fibres were of the type described in WO93/12275 to Courtaulds and sold as a fibrous dressing in the product AQUACEL ex ConvaTec. The fibres were then separately weighed and crimped. The fibres were then fed into an opening machine in the ratio 70% alginate fibre and 30% modified cellulose fibre to produce opened mixed fibre. The mixture was then fed to a hopper of a delivery device set to deliver the mixture to a carding machine so that it yielded carded web in the density range 70 to 240 gsm. From the carding machine the fibre web was taken and cross-lapped prior to being needle punched and rolled-up. The resulting product was a homogeneous blend of fibres that was soft to the touch and of good integrity.

EXAMPLE 2

The fluid uptake of a dressings according to the invention was measured by immersing the dressings totally in a bath of Solution A or of water for five minutes total immersion time and then removing the dressings, allowing them to drain for 30 seconds and then weighing. Fluid uptake was measured for a dressing (Dressing A) according to example 1 above, a dressing (Dressing B) prepared by the method of Example 1 using the fibres of Example 1 except that the ratio of alginate to cellulosic fibres was 60% alginate to 40% modified cellulose and as a control a dressing containing 100% modified cellulose fibres as used in Example 1.

| 5 cm × 5 cm Dressing | Water | Solution A |
|---|---|---|
| Dressing B initial weight | 0.3004 | 0.3021 |
| final weight (g) | 12.5956 | 6.3350 |
| difference | 12.2952 | 6.0329 |
| % difference | 40.93 | 19.97 |
| Dressing A initial weight | 0.1812 | 0.1646 |
| final weight (g) | 9.2720 | 4.4701 |
| difference | 8.0908 | 4.3055 |
| % difference | 44.65 | 26.16 |
| Control (100% modified cellulose) initial weight | 0.2349 | 0.2219 |
| final weight (g) | 7.0205 | 5.1444 |
| difference | 6.7856 | 4.9225 |
| % difference | 28.89 | 22.18 |

These results clearly show the increased absorbency of dressings according to the invention.

What is claimed is:

1. A wound dressing comprising a discrete modified cellulose gel forming fibre having a first absorbency rate and an alginate discrete gel forming fibre having a second absorbency rate, wherein said first absorbency rate differs from said second absorbency rate, and wherein said cellulose and alginate gel forming fibres are mixed together.

2. A wound dressing as claimed in claim 1 wherein the dressing is in sheet form.

3. A wound dressing as claimed in claim 1 wherein the dressing comprises a wound contacting surface consisting of a mixture of discrete modified cellulose fibres with at least one other type of discrete gel forming fibres.

4. A wound dressing as claimed in claim 1 wherein the dressing comprises a mixture of from 50% to 95% discrete alginate fibres and 5% to 50% discrete modified cellulose fibres by weight.

5. A wound dressing as claimed in claim 4 wherein the dressing comprises a mixture of from 65% to 80% discrete alginate fibres and 20% to 35% discrete modified cellulose fibres by weight.

6. A wound dressing as claimed in claim 5 wherein the dressing comprises a mixture of from 30% discrete modified cellulose fibres and 70% discrete alginate fibres by weight.

7. A wound dressing as claimed in claim 1 wherein the gel forming fibres have an absorbency of at least 2 g of liquid per g of fibre.

8. A method for the treatment of a wound comprising placing a wound dressing as claimed in claim 1 in direct contact with the wound.

9. A method for the treatment of a wound comprising placing a wound dressing as claimed in claim 4 in direct contact with the wound.

10. A method for the treatment of a wound as claimed in claim 9 wherein the wound is a chronic wound.

* * * * *